United States Patent [19]

LaCourse et al.

[11] Patent Number: 5,375,610

[45] Date of Patent: Dec. 27, 1994

[54] APPARATUS FOR THE FUNCTIONAL ASSESSMENT OF HUMAN ACTIVITY

[75] Inventors: John R. LaCourse, Durham; Paul Corcoran, Hancock, both of N.H.

[73] Assignee: University of New Hampshire, Durham, N.H.

[21] Appl. No.: 875,093

[22] Filed: Apr. 28, 1992

[51] Int. Cl.$^5$ ............................................. A61B 5/103
[52] U.S. Cl. ..................................... 128/782; 33/512
[58] Field of Search ....................... 128/782, 781, 774;
33/511, 512

[56] References Cited

U.S. PATENT DOCUMENTS

| | | | |
|---|---|---|---|
| 4,016,868 | 4/1977 | Allison | 128/644 |
| 4,444,205 | 4/1984 | Jackson | 128/782 |
| 4,557,275 | 12/1985 | Dempsey, Jr. | 128/782 |
| 4,583,554 | 4/1986 | Mittelman et al. | 128/774 |
| 4,665,928 | 5/1987 | Linial et al. | 128/782 |
| 4,699,156 | 10/1987 | Gracovetsky | 128/781 |
| 4,729,377 | 3/1988 | Granek et al. | 128/639 |
| 4,730,625 | 3/1988 | Fraser et al. | 128/781 |
| 4,922,925 | 5/1990 | Crandall et al. | 128/782 |
| 4,986,280 | 1/1991 | Marcus et al. | 128/774 |
| 5,012,819 | 5/1991 | Marras et al. | 128/781 |
| 5,099,846 | 3/1992 | Hardy | 128/653.1 |

FOREIGN PATENT DOCUMENTS

| | | | |
|---|---|---|---|
| 628936 | 10/1978 | U.S.S.R. | 128/782 |
| 733653 | 5/1980 | U.S.S.R. | 128/782 |

OTHER PUBLICATIONS

Brugger et al., "Computer-aided tracking of body sensor" Med. & Biol. Eng. & Comput. vol. 16, No. 12, pp. 207–210, Mar. 1978.

Primary Examiner—Stephen C. Pellegrino
Assistant Examiner—Guy V. Tucker
Attorney, Agent, or Firm—William B. Ritchie

[57] ABSTRACT

An apparatus for the functional assessment of human activity. The invention comprises four major components: the data acquisition unit, a body suit interface unit, a body suit having a plurality of mercury switches and a graphics oriented software package. The body suit is made from a non-conductive material, preferably a thermalactyl material with sensors permanently attached in position corresponding to the movements to be measured. The sensors have no direct electrical contact with the human wearer thus permitting the measurement period to extend to many hours. A portable data acquisition unit which is connected to the sensors enables the system to be used "on the job" to obtain mobility measurements under actual conditions. A graphic analysis means, connected to said data acquisition means, is provided for providing a visual display of the length of time that the human has spent in each of the pre-determined positions and the range of motion measured by the data acquisition unit. The system is especially useful in rehabilitation programs for quantifying the extent of mobility to select practical occupational alternatives.

10 Claims, 8 Drawing Sheets

APPARATUS FOR THE FUNCTIONAL ASSESSMENT OF HUMAN ACTIVITY

BACKGROUND OF THE INVENTION

1. Field of the Invention

Invention relates to quantitative measurements of the functional activity of human beings.

2. Description of the Related Art

All rehabilitation professionals share a need to measure outcome and produce "hard data" on the effectiveness of the therapy. Most of the available instruments described in the literature are pencil and paper questionnaires, which give a qualitative measure on dependence in specific activities.

Rehabilitation programs and facilities need a way to measure objectively the extent of physical activity of the mentally and physically disabled. This appraisal of functional status can be used to find compatible occupations allowing for specific impairments. Available measuring devices measure limited aspects of daily functioning, but no prior art instrument is available that records the overall pattern of daily physical activities using mobility and motion criteria.

Representative of the prior art is U.S. Pat. No. 4,729,377, issued to Church et al. on Mar. 8, 1988, which discloses a garment containing multiple conductive paths made of conductive cloth. The invention is used to contact an external electrical apparatus to various points on the skin for monitoring by soaking the site with conducting fluid. As shown in the advertising materials of Bio-Stimu Trend Corp., the assignee of the above-referenced patent, the invention is designed to measure activity in isolated joints or limbs. Moreover the use of conducting fluid for electrode connection makes the invention inappropriate for long term wearing use or a total body measurement of activity.

U.S. Pat. No. 4,862,896, issued to Greenwold et al. on Sep. 5, 1989, discloses a heart monitoring device for use under emergency conditions. Again, this device makes use of electrodes that are placed next to the skin requiring a fluid or paste to establish electrical conduction for the measurement of activity.

A more invasive technique is disclosed in U.S. Pat. No. 4,685,466, issued to Rau on Aug. 11, 1987. Rau discloses a measuring sensor using a plurality of short needle points to penetrate into the uppermost cell layers of the horny skin. The sensor is retained by means of a preferable flexible mounting. A quasi-invasive technique is not conducive to long term wearing nor able to quantify the electro-physiological parameters for an entire body.

Still another method for measuring the electrical activity in a patient's body is disclosed in U.S. Pat. No. 4,354,509, issued to Strahwald et al. on Oct. 19, 1982. This invention features an electrode system comprising flexible formed parts. In this disclosure, the contacting agent is a fleece material with an external contour slightly greater than the exterior perimeter of the formed part of the electrode system. As in the previously discussed disclosures, the concept is to make electrical contact with the skin of the patient.

The Social Security Administration recognized the strong need to develop techniques that would improve the lifestyles and working conditions of the physically challenged population. Olander et al. (Olander B. Walker, and G. Prazak, "An Agenda for Excellence," *Journal of Rehabilitation*, pp. 17-18, Mar. 1990) discussed this object in their publication "An Agenda for Excellence". The authors point out the need to improve the quality of current rehabilitation programs that are designed to place physically challenged persons into the workforce. In their study of rehabilitation programs throughout the country, they found that the top programs had a fifty percent successful placement ratio. In contrast, the worst programs achieved only a sixteen percent successful placement. One of the problems was considered to be a "lack of sufficient objective data to help evaluate the efficiency and effectiveness of their approaches". In a paper entitled "Vocational Evaluation in Supported Employment" by Rogan and Hagner (P. Rogan and D. Hagner, "Vocational Evaluation in Supported Employment," *Journal of Rehabilitation*, pp. 45-50, Mar. 1990), the authors discuss the criteria for vocational evaluation comprising "(a) describing an individual by his or her functioning needs, (b) specifying the outcomes to be achieved through rehabilitation, and (c) identifying the interventions and services required to achieve those outcomes". They concluded that "the context in which assessment occurs should be a primary importance. That is, behavior should be assessed within the same settings in which it is ultimately expected to occur."

A few devices have been developed which measure limited body movements. A wheelchair odometer, developed by Halstead et al. (L.S. Halstead, "Longitudinal Unobtrusive Measurements in Rehabilitation," *Arch. Phys. Med. Regabil.*, vol. 57, pp. 189-193, 1976), measures distances traveled by wheelchair bound persons. Halstead (L.S. Halstead et al., "Spinal Cord Injury: Time Out of bed During Rehabilitation," *Arch. Phys. Med. Rehabil.*, vol. 60, pp. 590-595, 1979) and Sanders (S. H. Sanders, "Toward a Practical Instrument System for the Automatic Measurement of "up-time" in Chronic Back Pain Patients," *Pain*, vol. 9, pp. 103-109, 1980) both explored the use of bed rest indicators that show how often a patient's bed was being occupied. A device capable of determining the amount of time spent in either a horizontal or vertical position, using a mechanical device attached to the trunk of the patient, was discussed by Bloom et al. (W. L. Bloom and M. F. Eidex, "Inactivity as a Major Factor in Obesity," *Metabolism*, vol. 16, pp. 679-684, 1967). LePorte et al. (R. E. LePorte et al., "An Objective Measure of Physical Activity for Epidemiology," *Res. Am J Epidemiol*, vol. 109, pp. 158-168, 1979) disclosed a surface EMG monitoring system that measures motor activity in human subjects. All of the above devices were insensitive to sleeping positions, physically cumbersome, difficult to wear and could be used for only a limited amount of time.

There have been many others who have concentrated their efforts on further analyzing back movement. Ortengren and Andersson (B. J. Anderson and D. B. Chaffin, *Occupational Biomechanics*. Wiley-Interscience, pp. 258-259, 1984) developed one such device which measures trunk flexion. The instrument consists of a pendulum potentiometer, a five level A to D converter, control circuits, and digital registers positioned onto a small harness to be worn on the back. This particular analyzer records amount of time spent in various intervals of forward flexion, as well as the number of times in and out of each interval. This device, however, is capable of measuring only forward trunk movements in the sagittal plane. Another device (. J. Anderson and D. B. Chaffin, Occupational Biomechanics. Wiley-Interscience, p. 138, 1984), the radio pill, is able to measure back movement. It is a pressure sensitive device that is swallowed. This procedure is expensive, intrusive and provides limited results.

Another approach disclosed by Brown, (L.P. Brown, "The Theory and Design of Piezoelectric/Pyroelectric Polymer Film Sensors for Biomedical Engineering Applications," *Biomedical Science Instrumentation*, vol. 25, pp. 119–126, 1989) uses piezo/pyroelectricity polymer film sensors. These sensors are capable of detecting numerical change in coordinates by detecting voltage fluctuations for a particular body location. The polymer film sensors tend to be capacitive, meaning that if a particular body position is held for a substantial length of time, the capacitive nature would result in loss of information.

None of the aforementioned devices are capable of measuring overall general body movement for an extended continuous time.

SUMMARY OF THE INVENTION

It is an object of the invention to provide a functional mobility assessment apparatus that measures and records gross human body movements up to a twenty-four hour time span.

It is another object of the invention to provide a functional mobility assessment apparatus that compares the body position profiles of disabled individuals to those of able-bodied individuals to identify possible job matches.

It is still another object of the invention to provide a functional mobility assessment apparatus system that is up to 93% accurate.

It is still another object of the invention to provide a functional mobility assessment apparatus that can measure and record more than a hundred body positions.

It is still another object of the invention to provide a functional mobility assessment apparatus that takes its measurements in a non-invasive manner.

It is still another object of the invention to provide a functional mobility assessment apparatus that incorporates a sensor studded body suit that can be worn comfortably for an extended period of time.

It is still another object of the invention to provide a quasi-real time emulation of functional mobility via a visual display.

It is a final object of the invention to provide a functional mobility assessment apparatus that incorporates graphic-oriented software aiding vocational rehabilitation counselors to determine the extent a client is able to preform a certain task.

The invention is an apparatus for the functional assessment of human activity. A body suit of non-conductive material that has a plurality of sensors is provided. The sensors have no direct electrical contact with said human. The sensors are attached to said suit in positions corresponding to the range of human motion to be measured. Data acquisition means, connected to said sensors, is provided for recording the gross body movements of said human over an extended period of time in a plurality of pre-determined positions. These positions correspond to positions occurring during normal daily activities. Graphic analysis means, connected to said data acquisition means, is provided for providing a visual display of the length of time that the human has spent in each of the pre-determined positions and the range of motion measured by said data acquisition means.

DETAILED DESCRIPTION OF THE INVENTION

The invention comprises four major components: the data acquisition unit, a body suit interface unit, a body suit having a plurality of mercury switches and a graphics oriented software package.

Figure 1:
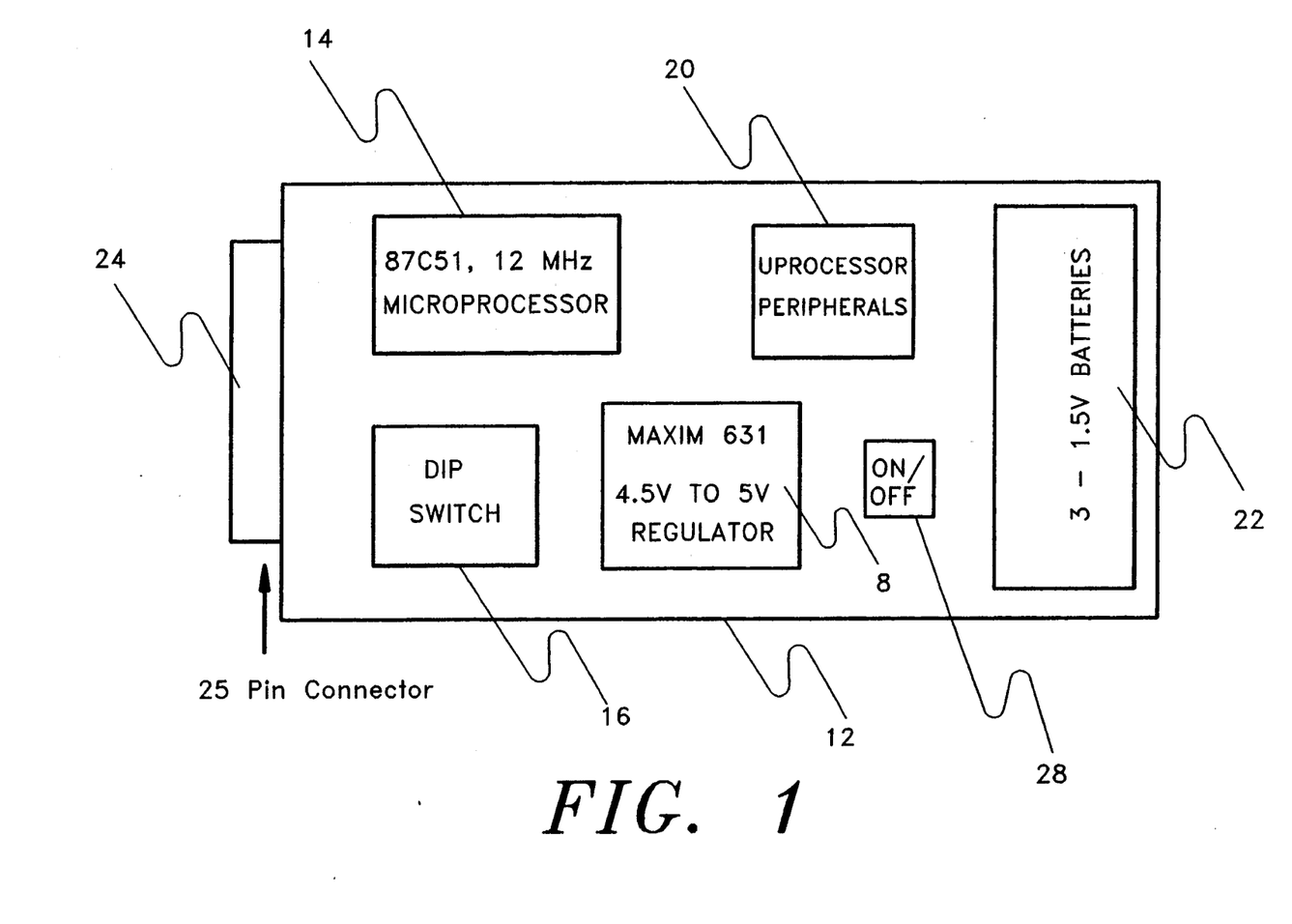
Fig. 1 is a block diagram of the data acquisition component of the invention.

FIG. 1 is a block diagram of the various component parts contained in the data acquisition unit. The preferred size of the box to contain all of the components shown in FIG. 1 measures 2.5 cm by 5.5 cm by 15 cm or approximately the same size as a video remote controller. The casing is a sliding two-piece unit made of hard plastic, durable enough to stand up to normal daily use.

Microprocessor 14 is preferably Intel 87C252. This microprocessor was chosen because it is a single chip computer system, eliminating the need for additional peripherals. Also this particular chip contains its own ROM, parallel and serial ports, RAM, timer and clock. In addition, the 87C252 is capable of sampling data every 1.32 seconds. The input and output data is fed through a 25 pin connector 24 linked to the 87C252. Microprocessor 14 is powered by three 1.5 V AA batteries shown in box 22 and regulated by a Maxim 631 4.5 V to 5 V step-up voltage regulator 8. Box 20 contains two 39 pF capacitors along with 12 MHz crystal to provide the clock-driven signals needed to regulate the system clock. Also included in that box are 150K resistor and 0.68 uF capacitor which produced the time constant for a system reset. Finally a series of 150K pullup resistors are needed to maintain port 0 set at wipe level '1'. Unit 12 also contains a low battery indicator and dip switch 16. The low battery indicator automatically shuts off the microprocessor 14 from sampling data and saves any data already collected. Microprocessor 14, using the dip switch 16, is capable of adjusting the sampling recording rate for increments of one, two or five seconds. On and Off switch 28 completes the features of unit 12.

Figure 2:
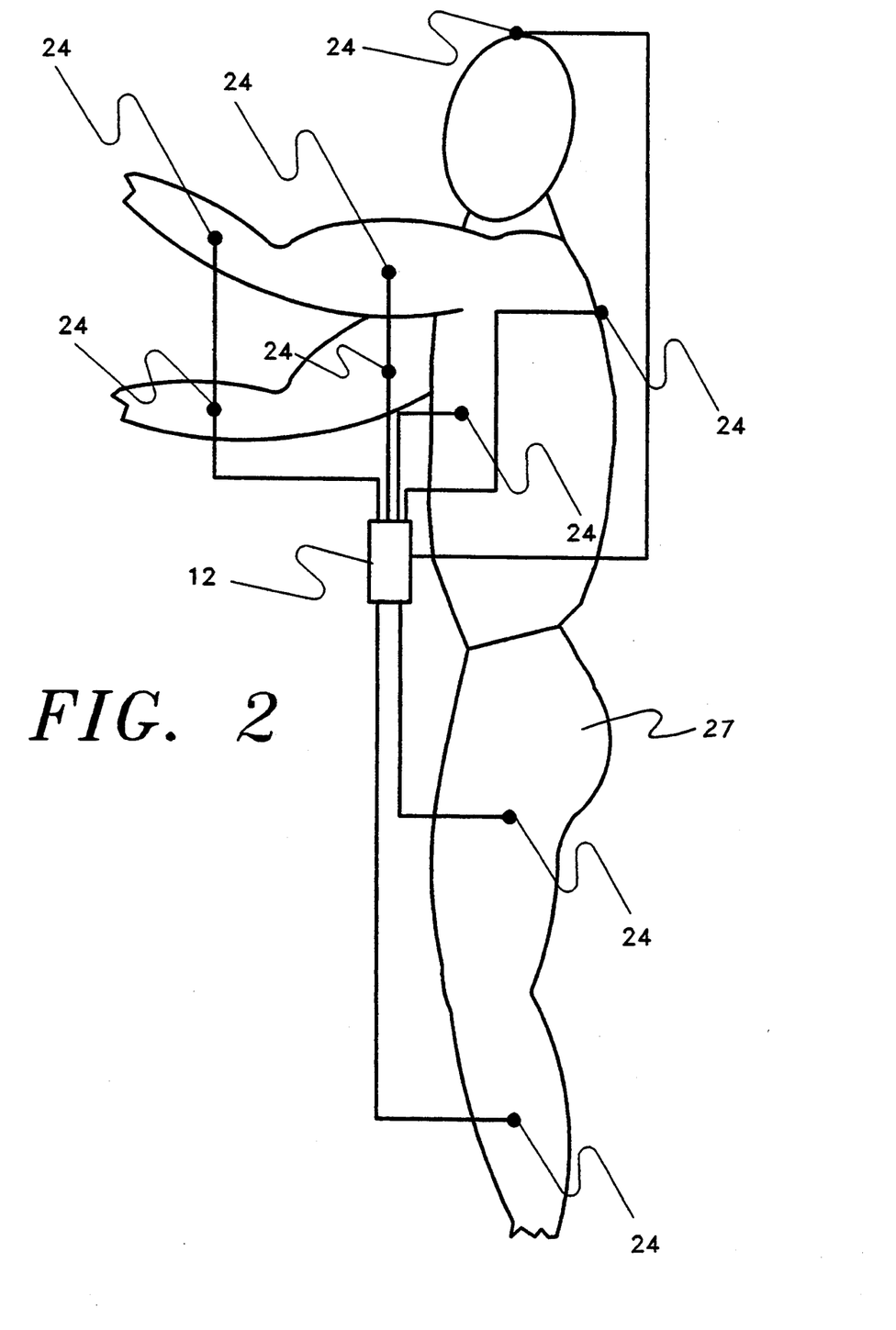
FIG. 2 is an illustration of the body suit component with representative body sensors positioned in accordance with the invention.

FIG. 2 shows the sensing system comprising body suit 27 and a plurality of sensors 24. Preferably sensors 24 are mercury switches shown located at various movement location points on the wearer. These positions may include the head, back, side, upper and lower arms and lower and upper leg. These sensors measure angles varying, for example, 45 degrees on the head sensor backward and forward, the upper arm measuring angles ranging from 45 degrees to 180 degrees to −45 degrees behind the back. The upper and lower leg sensors are used in determining various sitting positions.

The preferred mercury switches are Signal Systems International, model number 2009. However, other switches could be substituted. Sensors 24 are capable of detecting incremental changes of 12 degrees.

The proper codes used to determine the various positions are programmed into the 87C252 microprocessor. Each body position is represented by an eight bit code.

The body suit 27 is preferably a 'thermalactyl' suit produced by Damart and can be worn as an undergarment. The suit, resembling long underwear, contains both long sleeved tops and bottoms. Design characteristics that were considered include stretchability, reusability, and wearer comfort. Since this suit was intended to be worn under regular work clothes under regular work conditions, the suit has to be cool and comfortable while remaining unobtrusive to the wearer. Other materials that could be used 'lycra' or 'spandex' material, 'fishnet', or 'stockings'. The sensors (mercury switches) 24 are attached to body suit 27 by means of velcro strips sewn to suit 27 on various points of attachment. However, it is anticipated that the commercial version of the body suit will have mercury sensing switches 24 and the corresponding cable system sewn into the body suit 27 itself to alleviate the time required to properly fit the wearer.

Figure 3:
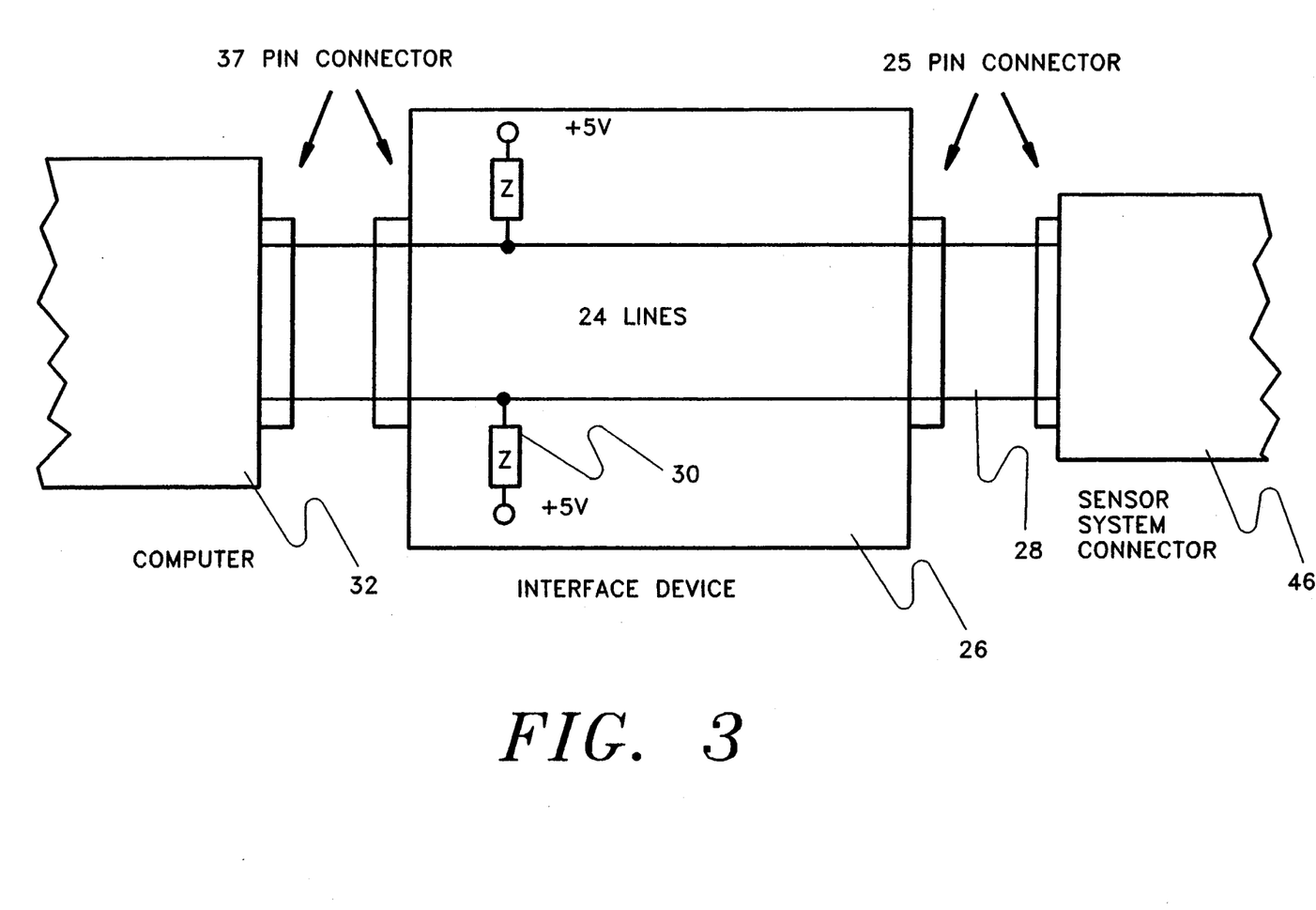
FIG. 3 is a block diagram of the body suit interface component of the invention.

FIG. 3 shows a block diagram for computer interface 26 between the computer 32 and body suit 27 with its mercury switches 24. Each of the 24 input lines 28 from the sensing system connector 46 are interfaced with a series of pull-up resistors 30 to ensure a proper reading by the computer, as the inputs from the mercury switches are low (grounded) and need to be raised to five volts in order to be detected by the computer. In addition to interface 26, a 24 line programmable A/D card, commercially available, must be installed in the computer 32 to allow the input to pass from sensing unit 12 to the computer 32. By connecting the body suit 27 directly to computer 32 via computer interface 26, body suit 27 can be calibrated and checked to be certain that it is functioning properly.

Figure 8:
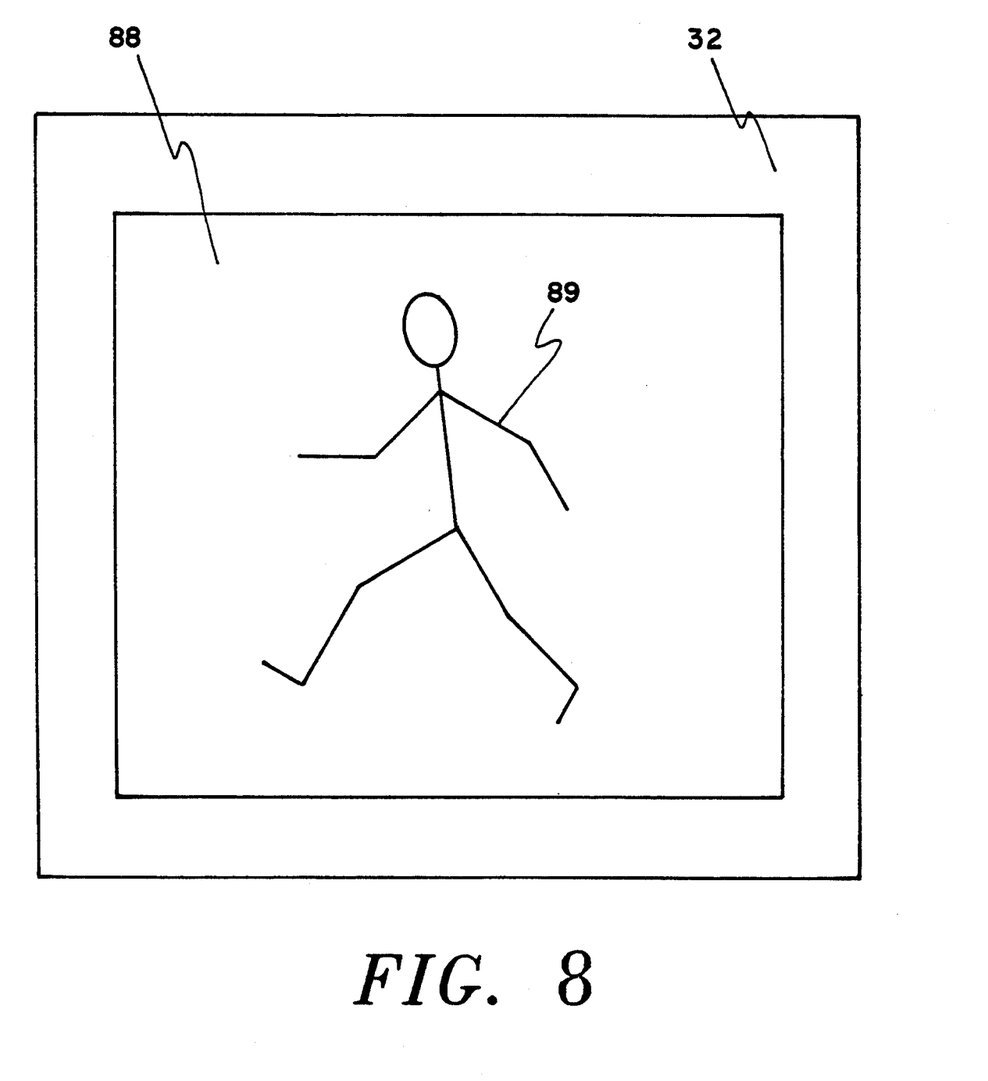
FIG. 8 is an illustration of the video display component of the invention.

The computer interface 26 also allows physical activity (mobility) to be shown on a computer 32 (video screen 88). This portion of the system is labeled the Real Time Emulator (RTE) as it shows an emulation of body and arm positions over time. It displays the body and arm positions, in real time, a stick FIG. 89 on the PC's video monitor 88. The RTE can be used for sensor testing, calibration, and movement feedback to the operator.

Figure 4:
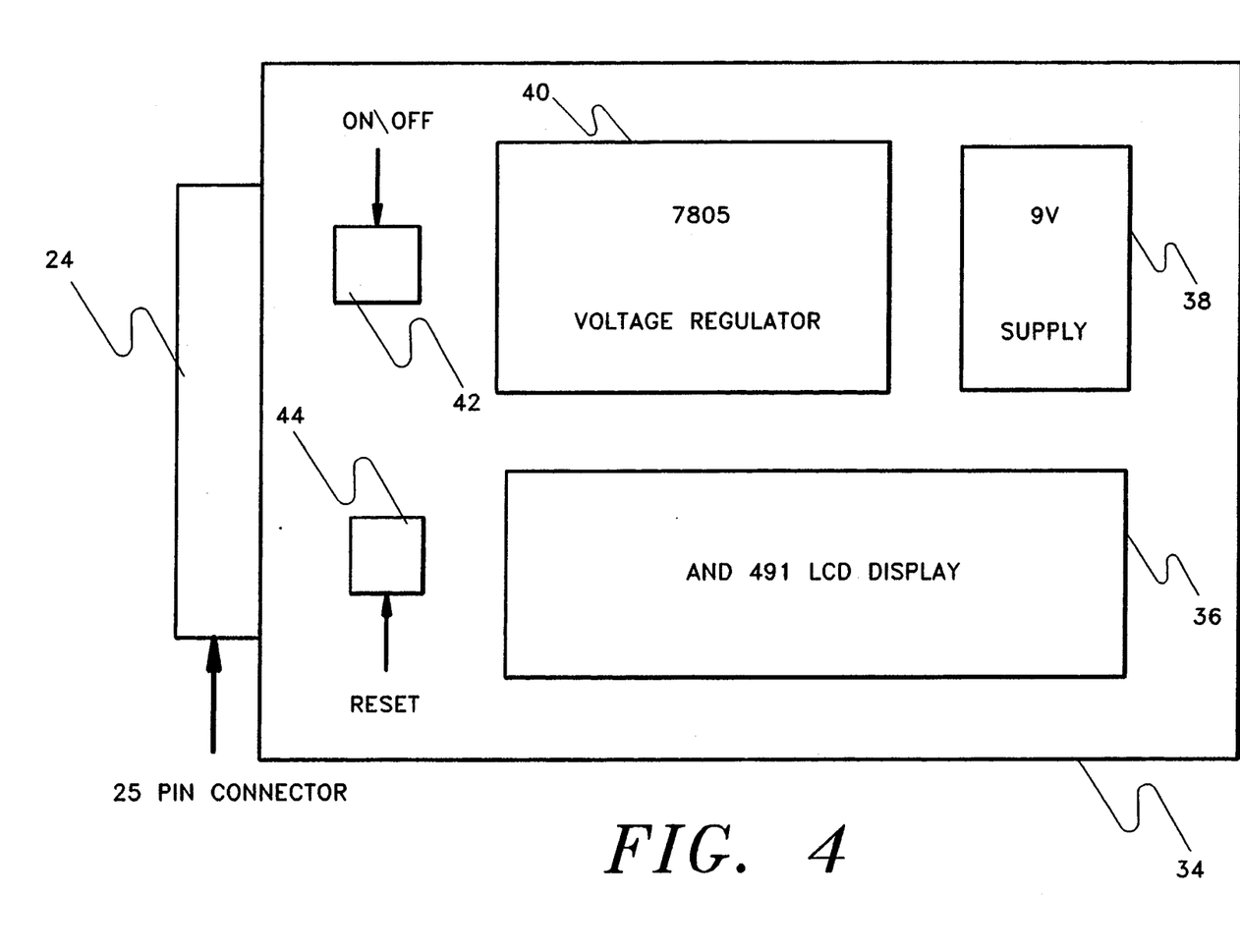
FIG. 4 is a block diagram of the digital display unit of the invention.

As shown in FIG. 4, a digital display unit 34 serves as an output mechanism for a data dump from the data acquisition unit 12. Display unit 34 is capable of displaying results recorded by the acquisition unit 12 during any period of testing. Display unit 34 provides the operator with feedback that includes testing time, time in a particular body position, and the number of changes in and out of that position, for all body positions programmed. This information allows the operator to determine the status of the system at any point during the measurement process.

LCD display 36 is preferably AND 491 LCD display which has a built-in microprocessor which will interface the microprocessor 14 of acquisition unit 12. Display 36 is capable of displaying two lines at a time, with sixteen characters per line. Display unit 36 is powered by a nine volt battery supply 38 which is stepped down to five volts by voltage regulator 40. Regulator 40 is preferably a part no. 7805 step down voltage regulator.

The display unit 34 interfaces with acquisition unit 12 via connector 24 which is a 25 pin connector. When unit 34 is connected to unit 12, unit 12 ceases to sample data and keep track of the length of time of the test, and instead, begins to transmit data in its download mode. Scroll pushbutton 42 causes unit 12 to advance through the body positions that have been recorded, one at a time. Reset button 44 is used to reset the microprocessor to take data again.

Figure 5:
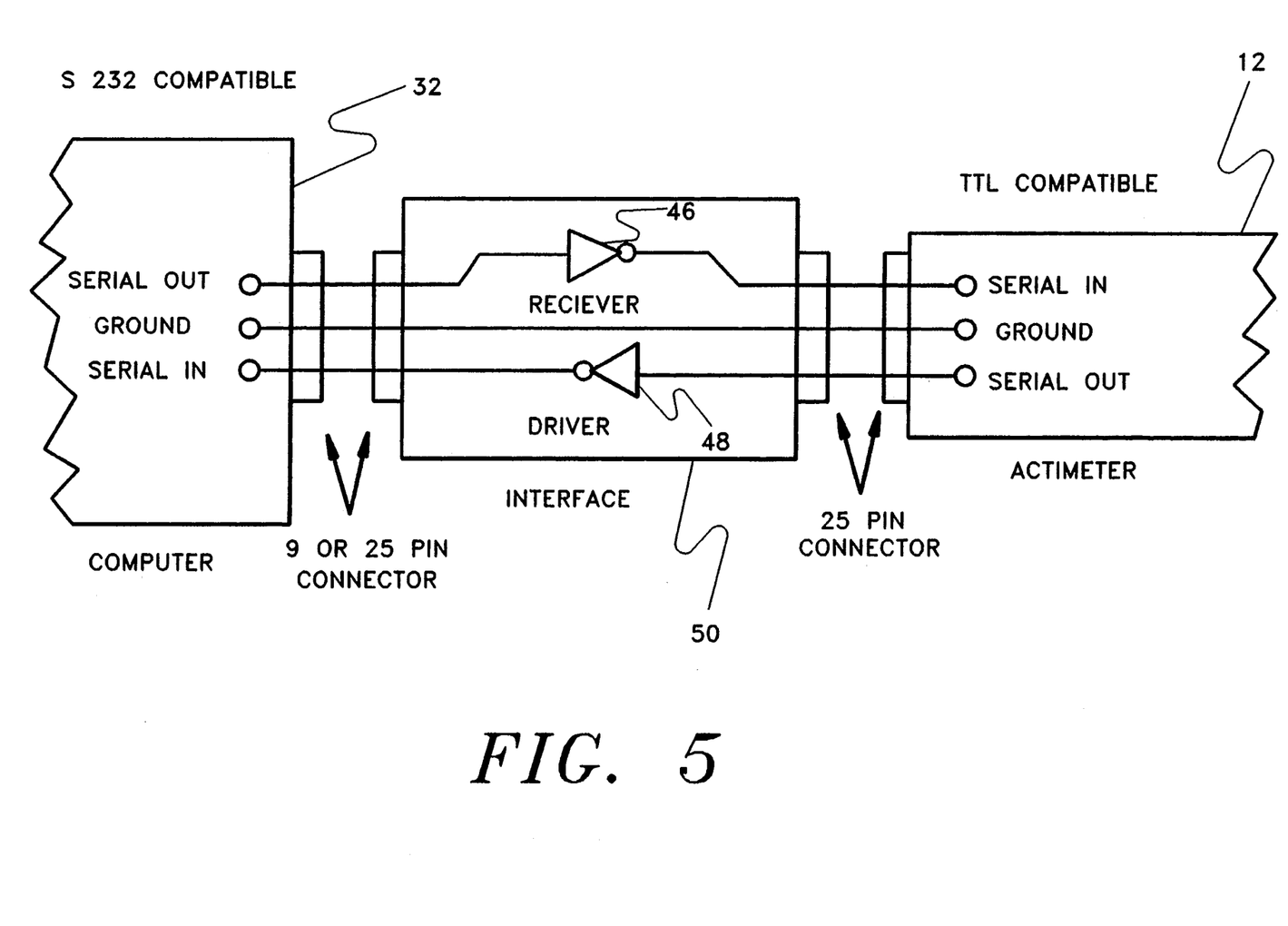
FIG. 5 is a block diagram of the interface required between the data acquisition unit and a personal computer in accordance with the invention.

FIG. 5 shows the additional hardware necessary for the interface between the data acquisition unit 12 and a personal computer 32 to run the computer analysis program described below. Interface 50 includes a receiver 46 and driver 48, enabling a conversion from TTL logic (data acquisition unit 12) to RS 232 capability (computer). Driver 48 and receiver 46 are preferably a chip such as the MAX 631 since it is only depends upon +5 volts for operation. At the data acquisition unit 12 end, a matching 25 pin connector is provided; at the computer end, either a 9 or 25 is used, depending upon the interface capabilities of the particular computer being used.

Figure 6:
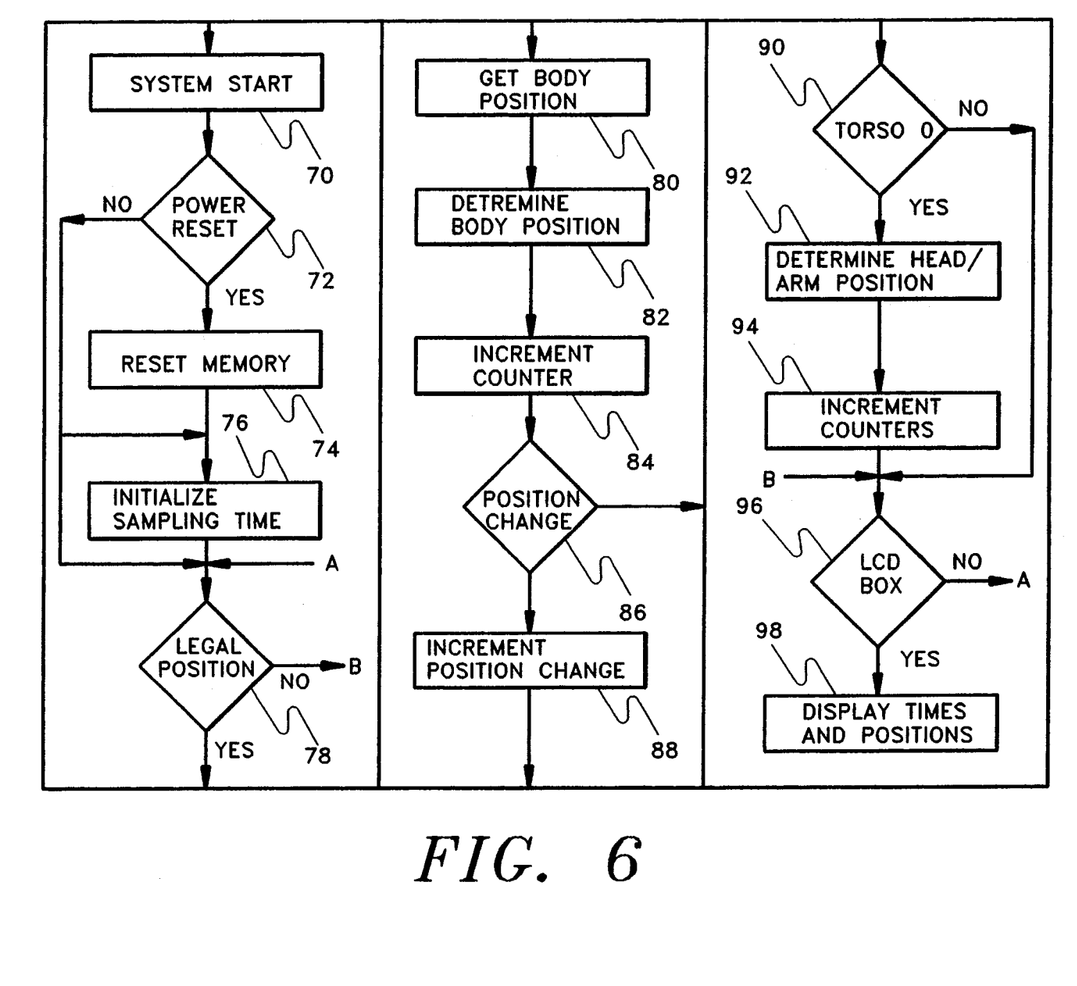
FIG. 6 is a flow chart block diagram of the steps in the control of the data acquisition unit.
Figure 7:
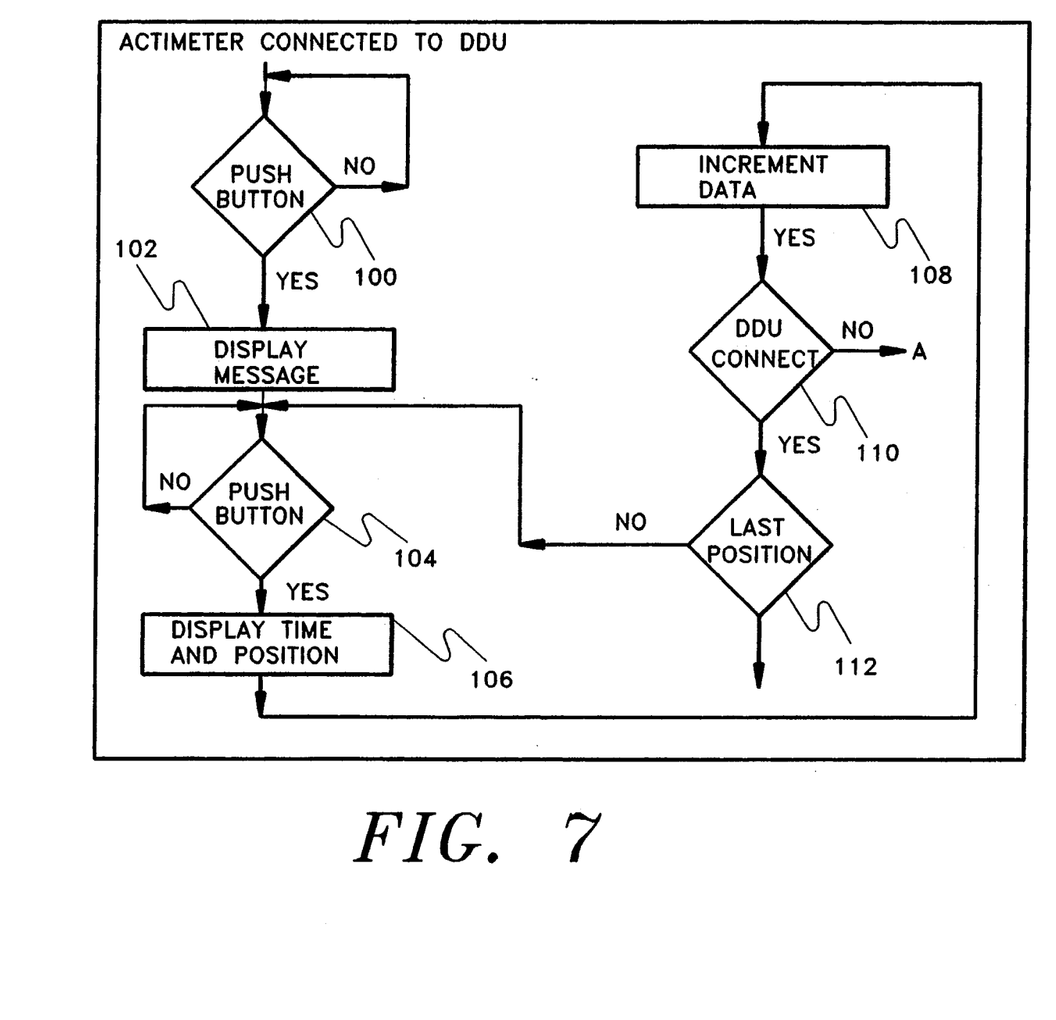
FIG. 7 is a flow chart diagram of the steps in the control of the digital display unit.

FIGS. 6 and 7 illustrate the graphics oriented software package which is the fourth major component of the system. FIG. 6 illustrates the steps in the software flow for the data acquisition unit 12. Step 70 is system start. Step 72 causes data acquisition unit 12 to continuously check to see if there has been a power reset. If there has, and this occurs when the power button 28 has been turned off and then on again, the memory inside microprocessor 14 is reset in step 74 and the sampling time is initialized to zero in step 76. If the system has not received a power reset, it continues to sample data based upon its initial sampling time. Next, the system detects what position it senses and determines if it is one of a plurality of pre-selected positions in step 78. The preferable number of total number of positions that can be sampled is in the neighborhood of ninety. However, this number can be adjusted up or down depending upon the particular measurement circumstances.

If the position is a pre-selected position as determined in step 78, then in step 80 that body position is obtained, and determined whether a body position has occurred. If one has occurred, then the position change indicator is incremented in step 86. The program then determines whether the wearer's torso is at 0 degrees. If it is, then the program determines what position the head and arms are in and increments their corresponding time in the position counters. Finally, the program continuously checks to determine whether it is connected to the digital display unit 34. If the connection is made, then unit 12 stops sampling data and enters into the download mode. The software continually loops through checking for various body positions and incrementing counters for various body positions and incrementing counters, until either a power reset occurs or the download mode is indicated.

The software flow chart for the digital display unit 34 is shown in FIG. 7. Digital display unit 34 enters into the download mode when the power reset is turned on and unit 12 is properly connected. The user begins operation of the digital display unit 34 by pressing button 42 as shown in step 100. Once pressed, a message is displayed by step 102 indicating the total sampling time for the test. The program then waits for button 42 to be pushed a second time in step 104. After receiving this input, the program directs, in step 106, the digital display unit 34 to display the first pre-selected position and the time spent in that position. Step 108 increments the address where that data has been stored. The program then checks to see whether that position was the last position to be displayed. If it was not, then the program will wait until button 42 is pushed again, thus displaying the next pre-selected position and its corresponding time, and so on, until all pre-selected positions have been displayed.

The program also continuously checks to see whether a power reset has occurred or if the data acquisition unit 12 has been disconnected. Once unit 12 is disconnected, then microprocessor 14 will return to its sampling mode of operation. Finally, after completing the loop of displayed pre-selected positions, the digital display unit 34 is re-initialized. Unit 34 will then display the introduction message along with the pre-selected body positions and their corresponding sampling times for as long as the operator continues to press pushbutton 42.

The operation of the computer program is accomplished by having each aspect of the analysis run directly off of the main program menu. The main program menu comprises nine different routines; Real-Time Emulator (RTE), Activity Option, Past Client, Position, Occupation, Graph, Analysis, Help, and Quit.

The RTE option emulates all the normal functions of the invention: samples the position sensors at a rate that is entered by the test administrator, determines the body and arm positions from the information obtained from the position sensors, stores the information for analysis (# of times the client entered a particular position and total time that the client was in a position), keeps track of elapsed time, and displays the body and arm positions, in real-time, as a stick figure on the computers video monitor.

The Activity option is used to retrieve data from the data acquisition unit 12 after a test is completed. Once selected, the program asks the user to connect the unit 12 to the interface device 26 and press any key to continue. The program then asks the user to type the name of the data file to be created, enabling the computer to read the data from the unit 12 and storing it into that data file, or else abort and return to the main program menu. After the data is printed to the data file, the program returns to the main program menu.

The Past Client prints out the data stored in a particular client's data file. The data file contains information regarding the amount of time one is in a particular position, created after the "Activity" routine has been successfully run. The data is printed onto the screen in a tabular format where it can be viewed or downloaded into a printer.

The Position option illustrates what the various body positions look like, graphically. On the top third of the screen is a body position graphics box, where stick figure representations of the different body positions are displayed. On the bottom two-thirds of the screen is a listing of the 112 body positions. Using the arrow keys, the user can highlight any one of the 112 body positions, and see its stick figure representation in the graphics box. This routine would enable the vocational rehabilitation counselor to get a feel for what the various types of body positions being detected by the invention look like.

The Occupation option lists twenty different occupations and their corresponding codes. The program asks the user to type the code of the occupation profile they wish to view. For example, if one wished to see the boiler attendant profile they would type '16' and press the return key. Once a number has been entered, the screen will display the list of 112 positions and their corresponding times for the particular occupation in question. Each occupation contains data files under the filename. The data for each occupation will be an overall average of the time spent in each position based upon data collected from the able-bodied population.

For example, perhaps five different able-bodied boiler attendants will perform the activities of their job while connected to the invention. Their data will then be averaged and stored in the data file for boiler attendants. The information in this data file may then be used to compare to the profile of a disabled person who is tested while performing the typical daily duties of a boiler attendant.

The Graph option allows the user to look at different types of data files from a choice of different graphing programs such as Client, Occupation, Overlay. The Client routine allows the operator to graph the activity profile of an individual client. The Occupation routine allows the user to graph a chosen occupational activity profile. The Overlay allows the operator to graph different entries on the same graph such as Client 1 and Client 2, Client 1 to Occupation 3, Client 1 today to Client 1 yesterday. There are three different types of graphs; vertical bar graph, horizontal bar graph, and line graph. Any graph routine can be sent to a printer. After the graph type is specified, the graph is plotted on the screen. Each graph plots the position number along the x-axis (horizontal), whose corresponding position is listed in both the program ("position") and the program documentation, and the corresponding time in that position along the y-axis (vertical), with units of seconds.

The Analysis option allows the user to compare the profile of a client's data file to that of any of the available occupation profiles or other client data files. The program will then display a table consisting of the various positions and the percentage of error between the data files. Also, the overall percentage of error, for all the body positions, is calculated and displayed at the bottom of the screen.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. An apparatus for the functional assessment of human activity comprising:
   a body suit of non-conductive material with a plurality of sensors having no direct electrical contact with a wearer of said suit and said sensors attached to said suit in positions corresponding to the range of the wearer's total body motion to be measured including limb position;
   data acquisition means, connected to said sensors, for recording the length of time the wearer has spent over an extended period of time in a plurality of pre-determined positions corresponding to positions occurring during normal daily activities; and graphic analysis means, connected to said data acquisition means, for providing a visual display of the length of time that the wearer has spent in each of the pre-determined positions and the range of motion measured by said data acquisition means;

graphic position means, connected to said graphic analysis means, for visually displaying representations of a human figure in each of the pre-determined positions;

occupational standards comparison means, connected to said graphic analysis means, for comparing the activity of the wearer including the length of time spent in each of the pre-determined positions during performance of said wearer's occupation; activity of able-bodied to humans including the length of time spent in each of the pre-determined positions while performing the same activities associated with that occupation.

2. The apparatus of claim 1 wherein graphic analysis means further comprises:

overlay means for overlaying in graphic form the tests results obtained from one test over the test results from another test.

3. The apparatus of claim 2 further comprising:

calibration interface means, connected between said body suit sensors and a digital computer, for calibrating said sensors.

4. The apparatus of claim 3 further comprising:

computer interface means, connected between said data acquisition means and said digital computer, for conversion of the data in said data acquisition means to a computer readable format.

5. The apparatus of claim 4 further comprising:

digital display unit means, connected to said data acquisition means, for displaying the data within said data acquisition means at any time during the testing of the wearer.

6. The apparatus of claim 5 wherein said sensors are mercury switches.

7. The apparatus of claim 6 wherein said digital display means further comprises an LCD display.

8. The apparatus of claim 7 wherein said computer interface means further comprises a receiver and a driver to convert TTL logic to RS 232 capability.

9. The apparatus of claim 8 wherein said data acquisition means further comprises a microprocessor.

10. The apparatus of claim 9 wherein said microprocessor is a single chip containing its own ROM, parallel and serial ports, RAM, timer and clock.

* * * * *